United States Patent
Zhu et al.

(10) Patent No.: US 7,022,695 B2
(45) Date of Patent: Apr. 4, 2006

(54) THIOETHER-SUBSTITUTED BENZAMIDES AS INHIBITORS OF FACTOR XA

(75) Inventors: Bing-Yan Zhu, Palo Alto, CA (US); Erick A. Goldman, Concord, CA (US); Wenrong Huang, Cupertino, CA (US); Penglie Zhang, Foster City, CA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 10/959,909

(22) Filed: Oct. 5, 2004

(65) Prior Publication Data

US 2005/0154204 A1 Jul. 14, 2005

Related U.S. Application Data

(60) Provisional application No. 60/510,264, filed on Oct. 9, 2003.

(51) Int. Cl.
C07D 213/75 (2006.01)
C07D 401/02 (2006.01)
C07D 401/14 (2006.01)
A61K 31/4427 (2006.01)
A61P 7/02 (2006.01)

(52) U.S. Cl. ............ 514/217.04; 514/218; 514/227.8; 514/235.8; 514/252.18; 514/318; 514/341; 514/343; 514/353; 540/575; 540/597; 544/60; 544/131; 544/360; 546/194; 546/272.7; 546/276.4; 546/306

(58) Field of Classification Search ............ 540/575, 540/597; 544/60, 131, 360; 546/194, 272.7, 546/276.4, 306; 514/217.04, 218, 227.8, 514/235.8, 252.18, 318, 341, 343, 353
See application file for complete search history.

(56) References Cited

U.S. PATENT DOCUMENTS

| 4,588,587 | A | 5/1986 | Gasic | |
|---|---|---|---|---|
| 6,376,515 | B1 * | 4/2002 | Zhu et al. | 514/318 |
| 6,835,739 | B1 * | 12/2004 | Zhu et al. | 514/318 |
| 2003/0069250 | A1 * | 4/2003 | Zhu et al. | 514/252.01 |
| 2004/0077690 | A1 * | 4/2004 | Zhu et al. | 514/346 |

FOREIGN PATENT DOCUMENTS

| EP | 0 798 295 A1 | 10/1997 |
|---|---|---|
| WO | 94/13693 A1 | 6/1994 |
| WO | 97/21437 A1 | 6/1997 |
| WO | 98/28269 A1 | 7/1998 |
| WO | 99/10316 A1 | 4/1999 |

OTHER PUBLICATIONS

Turpie, Am. J. Health Syst. Pharm., 60(22 Suppl. 7), S20-4, Nov. 15, 2003.*
Gresele et al., Trends in Pharmacological Sciences, 23(1), 25-32, Jan. 2002.*
Tan et al., Expert Opin. Investig. Drugs, 12(5), 799-804, 2003.*
Berge, S.M. et al., "Pharmaceutical Salts" J. Pharmac. Sci. 66:1-19 (1977).
Cheng, Y. et al., "Relationship between the inhibition constant (Ki) and the concentration of inhibitor which causes 50 per cent inhibition (I50) of an enzymatic reaction" Biochem. Pharmacol. 22(23):3099-108 (1973).
Claeson, G., "Synthetic peptides and peptidomimetics as substrates and inhibitors of thrombin and other proteases in the blood coagulation system" Blood Coag. Fibrinol. 5:411-436 (1994).
Elodi et al., "Optimization of conditions for the catalytic effect of the factor IXa-factor VIII complex: probable role of the complex in the amplification of blood coagulation" Thromb. Res. 15:617-629 (1979).
Finlayson, K. et al., "[3H]dofetilide binding to HERG transfected membranes: a potential high throughput preclinical screen" European J. Pharmacol. 430:147 (2001).

(Continued)

Primary Examiner—Fiona T. Powers
(74) Attorney, Agent, or Firm—Townsend and Townsend and Crew LLP

(57) ABSTRACT

Thioether-substituted benzamide compounds having the formula:

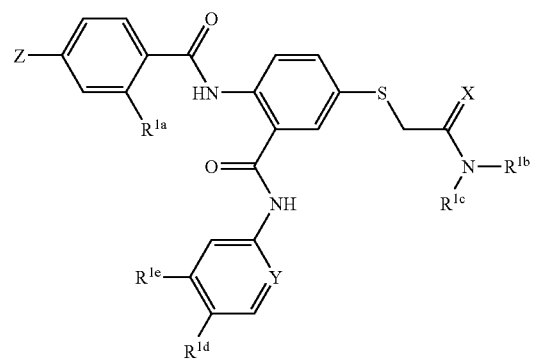

are provided that exhibit exceptionally strong inhibition of Factor Xa in combination with weak hERG binding.

30 Claims, No Drawings

OTHER PUBLICATIONS

Hautmann, J. et al., "Comparison of the anticoagulant and antithrombotic effects of synthetic thrombin and factor Xa inhibitors" Thromb. Haemost. 63:220-223 (1990).

Haverkamp, W. et al., "The potential for QT prolongation and pro-arrhythmia by non-anti-arrhythmic drugs: clinical and regulatory implications. Report on a Policy Conference of the European Society of Cardiology" Cardiovasc. Res. 47:219-33 (2000).

Hitomi, Y. et al., "Inhibitory effect of new syntheic protease inhibitor (FUT-175) on the coagulation system" Haemostasis 15:164-168 (1985).

Kam, C. et al., "Mechanism based isocoumarin inhibitors for trypsin and blood coagulation serine proteases: New anticoagulants" Biochemistry 27:2547-2557 (1988).

Kuzmic, P. et al., "High-throughput screening of enzyme inhibitors: Automatic determination of tightbinding inhibition constants" ANal. Biochem. 281:62-67 (2000).

Netzer, R. et al., "Screening lead compounds for QT interval prolongation" Drug Discovery Today 6:78-84 (2001).

Nutt, E. et al., "The amino acid sequence of antistasin, a potent inhibitor of factor Xa reveals a repeated internal structure" J. Biol. Chem. 263:10162-10167 (1988).

Pearlstein, R. et al., "Characterization of HERG potassium channel inhibition using CoMSIA 3D QSAR and homology modeling approaches" Bioorg. Med. Chem. Lett. 13:1829-35 (2003).

Redfern, W. et al., "Relationships between preclinical cardiac electrophysiology, clinical QT interval prolongation and torsade de pointes for a broad range of drugs: evidence for a provisional safety margin in drug development" Cardiovasc. Res. 58:32-45 (2003).

Sturzebecher, J. et al., "Synthetic inhibitors of bovine factor Xa and thrombin. Comparison of their anticoagulant efficiency" Thromb. Res. 54:245-252 (1989).

Tidewell, R. et al., "Strategies for anticoagulation with synthetic protease inhibitors. Xa versus thrombin inhibitors" Thromb. Res. 19:339-349 (1980).

Turner, A. et al., "p-Amidino esters as irreversible inhibitors of factor IXa and Xa and thrombin" Biochemistry 25:4929-4935 (1986).

Waxman, L. et al., "Tick anitcoagulant peptide (TAP) is a novel inhibitor of blood coagulation factor Xa" Science 248:593-596 (1990).

Zhou, Z et al., "Properties of HERG stably expressed in HEK293 cells studied at physiological tempurature" Biophys. J. 74:230-241 (1998).

* cited by examiner

US 7,022,695 B2

THIOETHER-SUBSTITUTED BENZAMIDES AS INHIBITORS OF FACTOR XA

CROSS-REFERENCES TO RELATED APPLICATIONS

This application claims the benefit of Provisional Patent Application Ser. No. 60/510,264, filed Oct. 9, 2003, the disclosure of which is hereby incorporated by reference.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

1. Field of the Invention

This invention relates to novel compounds which are potent and highly selective inhibitors of isolated factor Xa or when assembled in the prothrombinase complex. These compounds show selectivity for factor Xa versus other proteases of the coagulation (e.g. thrombin, fVIIa, fIXa) or the fibrinolytic cascades (e.g. plasminogen activators, plasmin). In another aspect, the present invention relates to novel monoamidino-containing compounds, their pharmaceutically acceptable salts, and pharmaceutically acceptable compositions thereof which are useful as potent and specific inhibitors of blood coagulation in mammals. In yet another aspect, the invention relates to methods for using these inhibitors as therapeutic agents for disease states in mammals characterized by coagulation disorders.

2. Background of the Invention

Hemostasis, the control of bleeding, occurs by surgical means, or by the physiological properties of vasoconstriction and coagulation. This invention is particularly concerned with blood coagulation and ways in which it assists in maintaining the integrity of mammalian circulation after injury, inflammation, disease, congenital defect, dysfunction or other disruption. Although platelets and blood coagulation are both involved in thrombus formation, certain components of the coagulation cascade are primarily responsible for the amplification or acceleration of the processes involved in platelet aggregation and fibrin deposition.

Thrombin is a key enzyme in the coagulation cascade as well as in hemostasis. Thrombin plays a central role in thrombosis through its ability to catalyze the conversion of fibrinogen into fibrin and through its potent platelet activation activity. Direct or indirect inhibition of thrombin activity has been the focus of a variety of recent anticoagulant strategies as reviewed by Claeson, G., "Synthetic Peptides and Peptidomimetics as Substrates and Inhibitors of Thrombin and Other Proteases in the Blood Coagulation System", *Blood Coag. Fibrinol.* 5:411–436 (1994). Several classes of anticoagulants currently used in the clinic directly or indirectly affect thrombin (i.e. heparins, low-molecular weight heparins, heparin-like compounds and coumarins).

A prothrombinase complex, including Factor Xa (a serine protease, the activated form of its Factor X precursor and a member of the calcium ion binding, gamma carboxyglutamyl (Gla)-containing, vitamin K dependent, blood coagulation glycoprotein family), converts the zymogen prothrombin into the active procoagulant thrombin. Unlike thrombin, which acts on a variety of protein substrates as well as at a specific receptor, factor Xa appears to have a single physiologic substrate, namely prothrombin. Since one molecule of factor Xa may be able to generate up to 138 molecules of thrombin (Elodi et al., *Thromb. Res.* 15:617–619 (1979)), direct inhibition of factor Xa as a way of indirectly inhibiting the formation of thrombin may be an efficient anticoagulant strategy. Therefore, it has been suggested that compounds which selectively inhibit factor Xa may be useful as in vitro diagnostic agents, or for therapeutic administration in certain thrombotic disorders, see e.g., WO 94/13693.

Polypeptides derived from hematophagous organisms have been reported which are highly potent and specific inhibitors of factor Xa. U.S. Pat. No. 4,588,587 describes anticoagulant activity in the saliva of the Mexican leech, *Haementeria officinalis*. A principal component of this saliva was shown to be the polypeptide factor Xa inhibitor, antistasin (ATS), by Nutt, E. et al., "The Amino Acid Sequence of Antistasin, a Potent Inhibitor of Factor Xa Reveals a Repeated Internal Structure", *J. Biol. Chem.,* 263:10162–10167 (1988). Another potent and highly specific inhibitor of Factor Xa, called tick anticoagulant peptide (TAP), has been isolated from the whole body extract of the soft tick *Ornithidoros moubata*, as reported by Waxman, L., et al., "Tick Anticoagulant Peptide (TAP) is a Novel Inhibitor of Blood Coagulation Factor Xa" *Science,* 248:593–596 (1990).

Factor Xa inhibitory compounds which are not large polypeptide-type inhibitors have also been reported including: Tidwell, R. R. et al., "Strategies for Anticoagulation With Synthetic Protease Inhibitors. Xa Inhibitors Versus Thrombin Inhibitors", *Thromb. Res.,* 19:339–349 (1980); Turner, A. D. et al., "p-Amidino Esters as Irreversible Inhibitors of Factor IXa and Xa and Thrombin", *Biochemistry,* 25:4929–4935 (1986); Hitomi, Y. et al., "Inhibitory Effect of New Synthetic Protease Inhibitor (FUT-175) on the Coagulation System", *Haemostasis,* 15:164–168 (1985); Sturzebecher, J. et al., "Synthetic Inhibitors of Bovine Factor Xa and Thrombin. Comparison of Their Anticoagulant Efficiency", *Thromb. Res.,* 54:245–252 (1989); Kam, C. M. et al., "Mechanism Based Isocoumarin Inhibitors for Trypsin and Blood Coagulation Serine Proteases: New Anticoagulants", *Biochemistry,* 27:2547–2557 (1988); Hauptmann, J. et al., "Comparison of the Anticoagulant and Antithrombotic Effects of Synthetic Thrombin and Factor Xa Inhibitors", *Thromb. Haemost.,* 63:220–223 (1990); and the like.

Others have reported Factor Xa inhibitors which are small molecule organic compounds, such as nitrogen containing heterocyclic compounds which have amidino substituent groups, wherein two functional groups of the compounds can bind to Factor Xa at two of its active sites. For example, WO 98/28269 describes pyrazole compounds having a terminal C(=NH)—NH$_2$ group; WO 97/21437 describes benzimidazole compounds substituted by a basic radical which are connected to a naphthyl group via a straight or branched chain alkylene, —C(=O) or —S(=O)$_2$ bridging group; WO 99/10316 describes compounds having a 4-phenyl-N-alkylamidino-piperidine and 4-phenoxy-N-alkylamidino-piperidine group connected to a 3-amidinophenyl group via a carboxamidealkyleneamino bridge; and EP 798295 describes compounds having a 4-phenoxy-N-alkylamidino-piperidine group connected to an amidinonaphthyl group via a substituted or unsubstituted sulfonamide or carboxamide bridging group.

Still further, drug-induced QT prolongation on hearts has been recently recognized to cause adverse and fatal side-effects in many clinical settings (Netzer, R., et al. *Drug*

Discovery Today, 6:78 (2001)). Several drugs were withdrawn from the market due to their hERG binding and attending QT interval prolongation, for example, Terfenadine (Seldane®), Cisapride (Propulsid®), and astemizole (Hismanal®)). See Pearlstein, R. A., et al., *Bioorg. Med. Chem. Lett.* 13:1829 (2003).

The hERG potassium channel is human ether-a-go-go-related gene that is expressed in the human heart, and is a key effector of cardiac repolarization, and contributes to the QT interval measured by ECG. It has been shown that inhibition of hERG potassium channel can lead to a prolongation of the QT interval, widely considered a critical risk factor for torsades de pointes (TdP) arrhythmia. Thus, hERG binding has been becoming a major hurdle in current drug development. Fortunately, the high throughput preclinical in vitro assays that measure compound's ability to inhibit hERG channel have become powerful screening tools for medicinal chemists to gain first hand SAR information and to evaluate their potential side-effect in early stage of drug discovery. See Haverkamp, W.; et al. *Cardiovasc. Res.* 47:219 (2000). Finlayson, K.; et al., *European Journal of Pharmacology* 430:147 (2001).

Significant progress has been made during the last few years, in the understanding of electrophysiology of hERG channels, mechanisms of drug-induced QT prolongation, the structural understanding of drugs binding to hERG channel, the relationship of hERG binding potency with preclinical in vivo QT prolongation studies (Redfern, W. S., et al., *Cardiovasc. Res.* 58:32 (2003)). Thus, it is highly desirable to find new compounds that provide beneficial anti-thrombotic activity with little or no hERG binding.

There exists a need for effective therapeutic agents for the regulation of hemostasis, and for the prevention and treatment of thrombus formation and other pathological processes in the vasculature induced by thrombin such as restenosis and inflammation. In particular, there continues to be a need for compounds which selectively inhibit factor Xa or its precursors. Compounds that have different combinations of bridging groups and functional groups than compounds previously discovered are needed, particularly compounds which selectively or preferentially bind to Factor Xa. Compounds with a higher degree of binding to Factor Xa than to thrombin are desired, especially those compounds having good bioavailability and/or solubility.

BRIEF SUMMARY OF THE INVENTION

In one aspect, the present invention provides compounds having the formula (I):

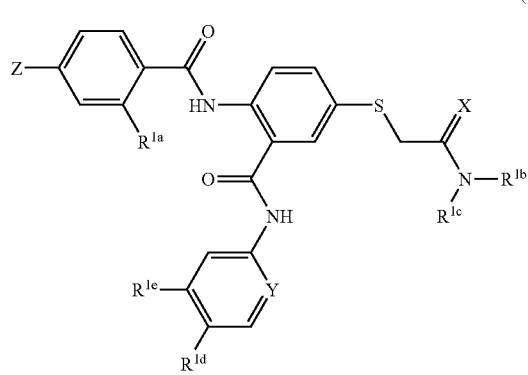

(I)

or a pharmaceutically acceptable salt thereof. In formula I, the symbol $R^{1a}$ represents H, halogen, hydroxy, $C_{1-6}$ alkyl, $C_{1-6}$ haloalkyl, $C_{1-6}$ alkoxy, $C_{1-6}$ haloalkoxy, $(C_{1-6}$ alkyl$)_{0-2}$amino or $C_{1-6}$ alkylcarbonyl; the symbols $R^{1b}$ and $R^{1c}$ independently represent H or $C_{1-6}$ alkyl, or optionally, $R^{1b}$ and $R^{1c}$ are combined with the nitrogen atom to which each is attached to form a 5-, 6- or 7-membered monocyclic ring having from 0 to 1 additional heteroatom ring members or an 8-, 9-, 10- or 11-membered bicyclic ring having 0–2 additional heteroatom ring members, the heteroatom ring members being selected from O, N, S, S(O) and S(O)$_2$, and the ring being further substituted with from zero to two substituents independently selected from $C_{1-6}$ alkyl, $(C_{1-6}$ alkyl$)_{0-2}$amino, oxo and an amine protecting group. The symbols $R^{1d}$ and $R^{1e}$ each independently represent H, halogen, hydroxy, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $(C_{1-6}$ alkyl$)_{0-2}$amino or amino$C_{1-6}$ alkyl; or $R^{1d}$ and $R^{1e}$ can be combined to form a fused 5–6 membered ring having 0–2 ring heteroatoms selected from N, O and S.

The letter X in formula I represents O or S or together with the carbon atom to which it is attached is CH$_2$. The letter Y in formula I represents CH or N; and the letter Z represents a group having the formula:

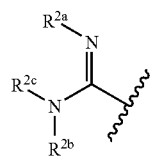

wherein the symbols $R^{2a}$, $R^{2b}$ and $R^{2c}$ each independently represent H, hydroxy, $C_{1-6}$ alkyl, $C_{3-6}$ cycloalkyl, $C_{1-6}$ alkoxy and $(C_{1-6}$ alkyl$)_{0-2}$amino; or optionally, any two of $R^{2a}$, $R^{2b}$ and $R^{2c}$ are taken together with their intervening atom(s) to form a 3-, 4-, 5-, 6- or 7-membered ring having from 0 to 1 additional heteroatom ring members selected from O, N, S, S(O) and S(O)$_2$, the ring being further substituted with from zero to two substituents independently selected from $C_{1-6}$ alkyl, hydroxy, $C_{1-6}$ alkoxy, CO$_2$H, oxo and $(C_{1-6}$ alkyl$)_{0-2}$amino.

In addition to the compounds of the present invention, pharmaceutical compositions are provided, along with methods for the treatment of conditions characterized by undesired thrombosis, such as acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, and conditions requiring the fitting of prosthetic devices.

BRIEF DESCRIPTION OF THE DRAWINGS

Not applicable.

DETAILED DESCRIPTION OF THE INVENTION

Definitions

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group is one having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$ cycloalkyl) and being fully saturated or having no more than one double bond between ring vertices. When "cycloalkyl" is used in combination with "alkyl", as in $C_{3-5}$cycloalkyl-alkyl, the cycloalkyl portion is meant to have from three to five carbon atoms, while the alkyl portion is an alkylene moiety having from one to three carbon atoms (e.g., —$CH_2$—, —$CH_2CH_2$— or —$CH_2CH_2CH_2$—).

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. For brevity, the term $C_{1-6}$alkylamino is meant to include straight chain, branched or cyclic alkyl groups or combinations thereof, such as methyl, ethyl, 2-methylpropyl, cyclobutyl and cyclopropylmethyl.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. Exemplary aryl groups are phenyl, naphthyl, biphenyl and the like. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of heteroaryl groups include 1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl 2-thienyl, 3-thienyl, 2-pyridyl, 3-pyridyl, 4-pyridyl, 2-pyrimidyl, 4-pyrimidyl, 5-benzothiazol purinyl, 2-benzimidazolyl, benzopyrazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers (e.g., separate enantiomers) are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

General

The present invention derives from the surprising discovery that compounds of formula I exhibit strong inhibition of Factor Xa, yet exhibit only weak hERG binding. Compounds having a reduced inhibition of hERG are less likely to cause the prolongation of the QT interval, which is associated with certain types of arrhythmia. Therefore, the present compounds are useful for the treatment or prophylaxis of undesired thrombosis while providing a lower risk of QT-related side effects.

DESCRIPTION OF THE EMBODIMENTS

Compounds

In one aspect, the present invention provides compounds having the formula (I):

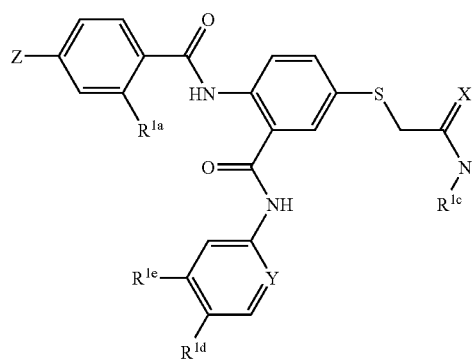

(I)

or a pharmaceutically acceptable salt thereof. In formula I, the symbol $R^{1a}$ represents H, halogen, hydroxy, $C_{1-6}$ alkyl, $C_{1-6}$ haloalkyl, $C_{1-6}$ alkoxy, $C_{1-6}$ haloalkoxy, $(C_{1-6}$ alkyl$)_{0-2}$amino or $C_{1-6}$ alkylcarbonyl. Preferably, $R^{1a}$ is H or halogen. The symbols $R^{1b}$ and $R^{1c}$ independently represent H or $C_{1-6}$ alkyl, or optionally, $R^{1b}$ and $R^{1c}$ are combined with the nitrogen atom to which each is attached to form a 5-, 6- or 7-membered monocyclic ring having from 0 to 1 additional heteroatom ring members or an 8-, 9-, 10- or 11-membered bicyclic ring having 0–2 additional heteroatom ring members, the heteroatom ring members being selected from O, N, S, S(O) and S(O)$_2$, and the ring being further substituted with from zero to two substituents independently selected from $C_{1-6}$ alkyl, $(C_{1-6}$ alkyl$)_{0-2}$amino, oxo and an amine protecting group. In one group of preferred embodiments, $R^{1b}$ and $R^{1c}$ are independently selected from H and $C_{1-4}$ alkyl. The symbols $R^{1d}$ and $R^{1e}$ each independently represent H, halogen, hydroxy, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $(C_{1-6}$ alkyl$)_{0-2}$amino or amino$C_{1-6}$ alkyl; or $R^{1d}$ and $R^{1e}$ can be combined to form a fused 5–6 membered ring having 0–2 ring heteroatoms selected from N, O and S. In certain preferred embodiments, $R^{1d}$ is selected from halogen, hydroxy, $C_{1-3}$ alkyl, $C_{1-3}$ haloalkyl, $C_{1-3}$ alkoxy and amino$C_{1-3}$ alkyl. In other preferred embodiments, $R^{1e}$ is hydrogen.

The letter X in formula I represents O or S or together with the carbon atom to which it is attached is CH$_2$. Preferably, X is O, or together with the carbon atom to which it is attached is CH$_2$. The letter Y in formula I represents CH or N, preferably N.

The letter Z represents a group having the formula:

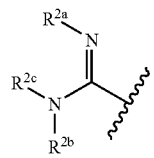

wherein the symbols $R^{2a}$, $R^{2b}$ and $R^{2c}$ each independently represent H, hydroxy, $C_{1-6}$ alkyl, $C_{3-6}$ cycloalkyl, $C_{1-6}$ alkoxy and $(C_{1-6}$ alkyl$)_{0-2}$amino; or optionally, any two of $R^{2a}$, $R^{2b}$ and $R^{2c}$ are taken together with their intervening atom(s) to form a 3-, 4-, 5-, 6- or 7-membered ring having from 0 to 1 additional heteroatom ring members selected from O, N, S, S(O) and S(O)$_2$, the ring being further substituted with from zero to two substituents independently selected from $C_{1-6}$ alkyl, hydroxy, $C_{1-6}$ alkoxy, CO$_2$H, oxo and $(C_{1-6}$ alkyl$)_{0-2}$amino. In preferred embodiments, Z is selected from

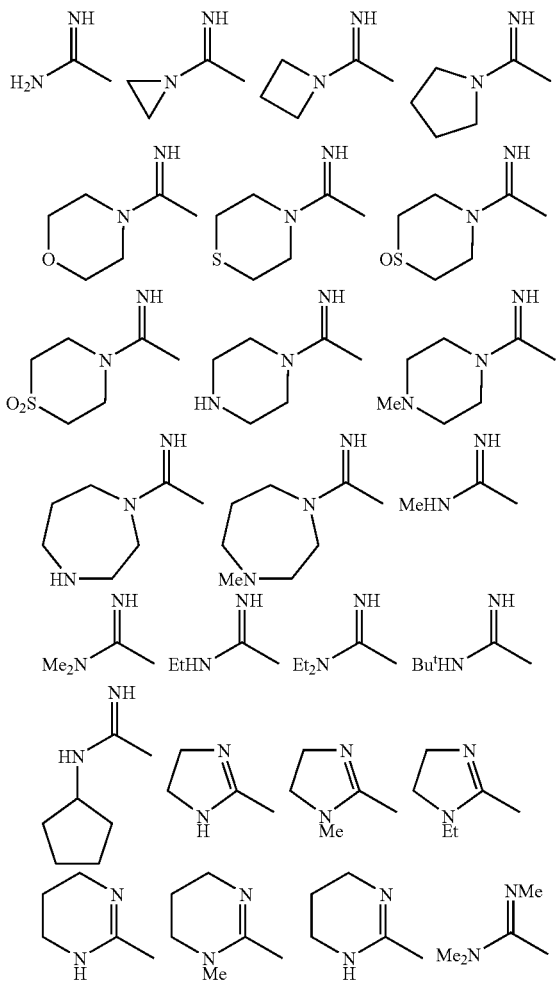

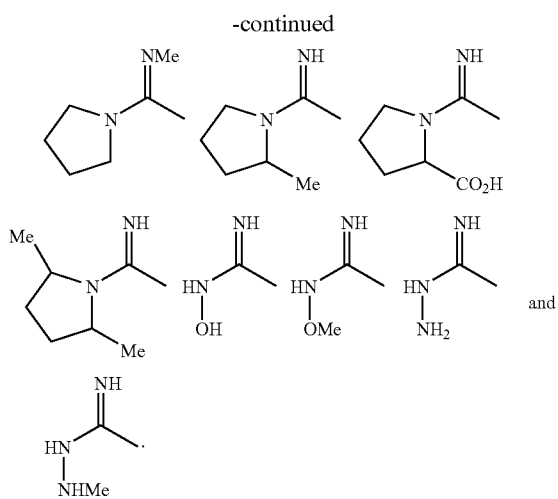

Certain combinations of X, Y, Z and $R^{1a}$ through $R^{1e}$ are also set forth as preferred embodiments.

In a first group of preferred embodiments, X is O and Z is selected from

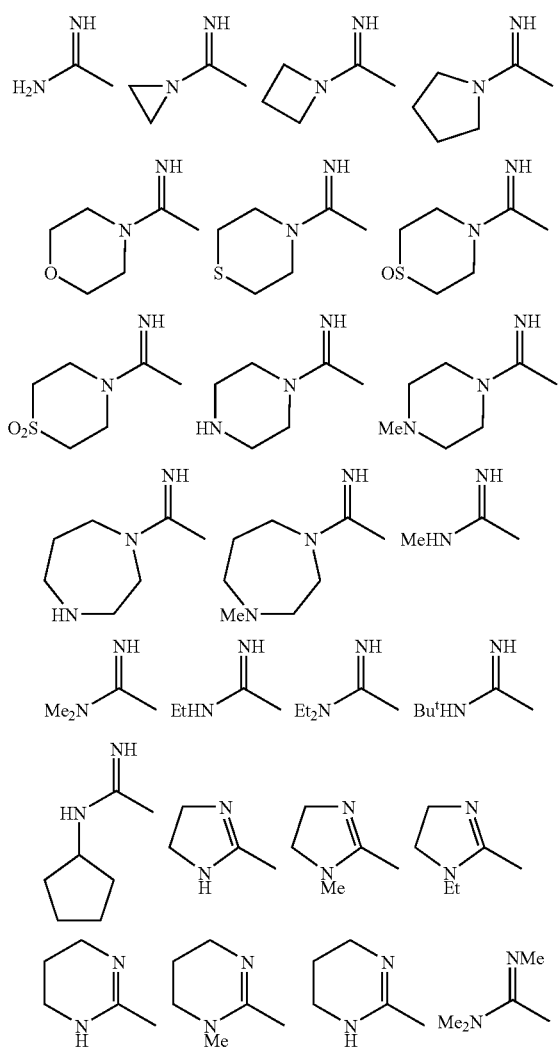

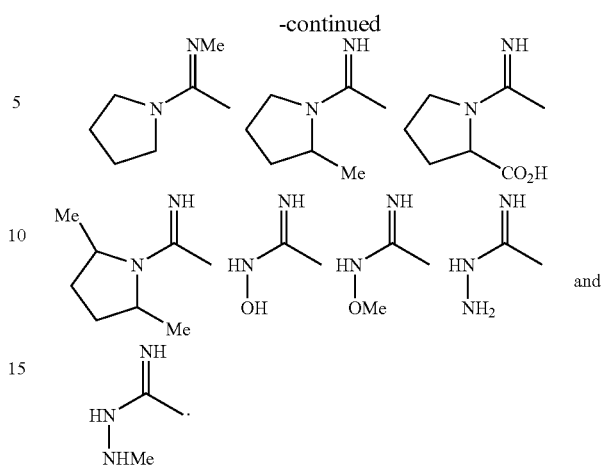

Within this first group of preferred embodiments, $R^{1b}$ and $R^{1c}$ are preferably H or $C_{1-3}$ alkyl, or are combined with the nitrogen atom to which each is attached to form a 5-, 6- or 7-membered ring having from 0 to 1 additional heteroatom ring members selected from O, N and S, wherein the ring is selected from pyrrolidine, piperidine, piperazine, morpholine, homopiperidine, homopiperazine and thiomorpholine. More particularly, the moiety $—N(R^{1b})(R^{1c})$ is preferably selected from

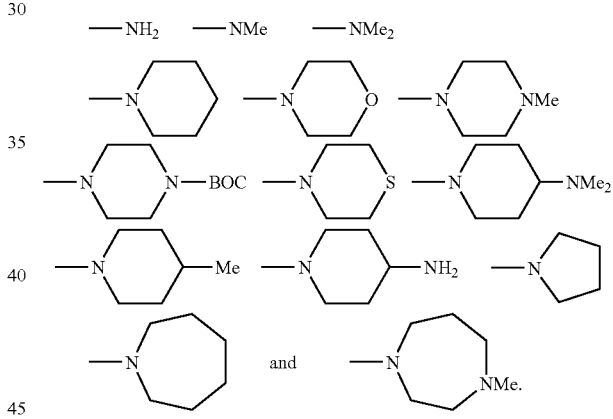

In still further preferred embodiments, $R^{1a}$ is preferably selected from H, F, Cl and Br; $R^{1d}$ is preferably —F, —Cl, —Br, —OCH$_3$, —OH, —CH$_3$, —CF$_3$ or —CH$_2$NH$_2$; and Y is preferably N.

In other preferred combinations in the first group, Z is preferably selected from

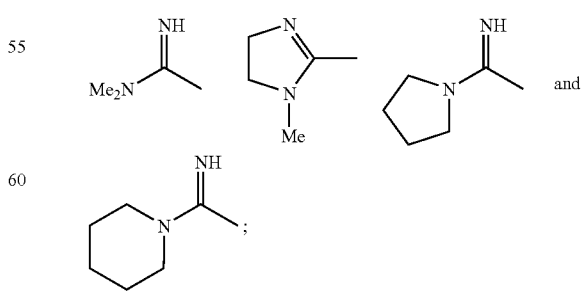

and the moiety $—N(R^{1b})(R^{1c})$ is preferably selected from

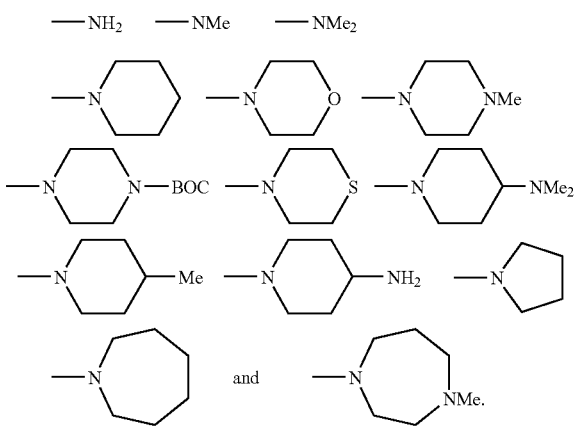

In a second group of preferred embodiments, X and the carbon atom to which it is attached is CH₂. Further preferred are those embodiments in which Z is selected from

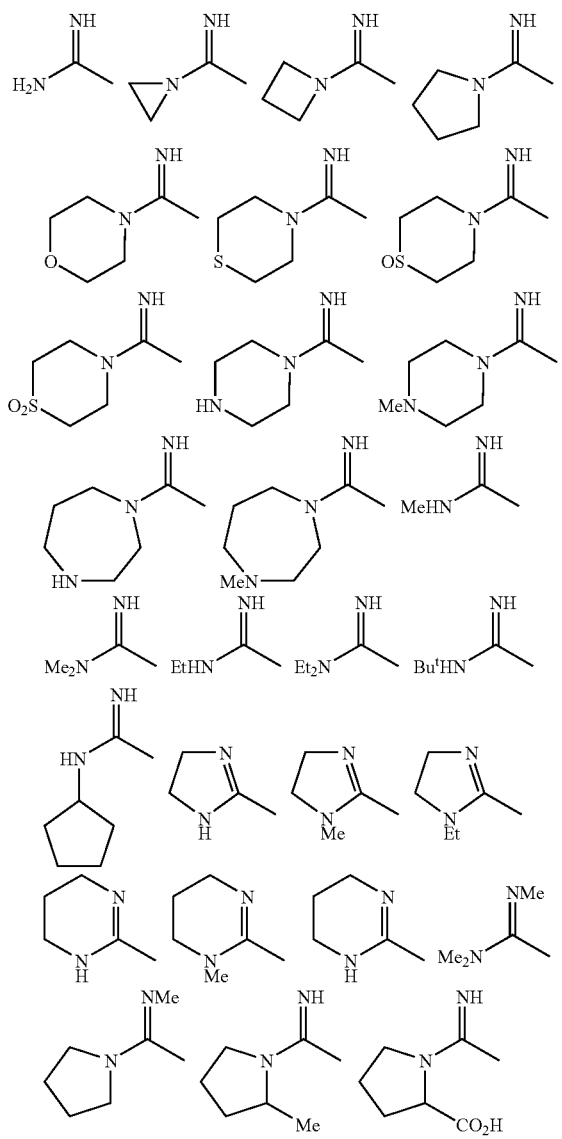

more preferably, Z is selected from

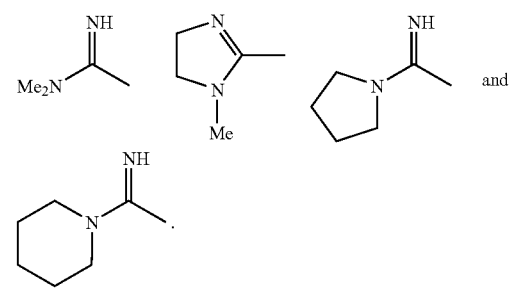

In still further preferred embodiments, the moieties —N($R^{1b}$)($R^{1c}$), $R^{1a}$, $R^{1d}$ and $R^{1e}$ are selected from the preferred groups provided with respect to the first group of preferred embodiments, or with reference to formula I, above.

Among the most preferred embodiments of the invention are the compounds provided in the Examples below.

Synthesis Methods

Schemes 1 and 2 illustrate methods for the preparation of compounds of formula I, exemplified by compounds viii and xii. One of skill in the art will appreciate that similar routes can be taken to prepare a number of related derivatives simply my substituting various reactant species. For example, replacing 2-amino-5-chloropyridine with other suitably substituted 2-aminopyridines provides compounds of formula I in which $R^{1d}$ and $R^{1e}$ are moieties such as alkyl, haloalkyl, alkoxy, alkylamino and the like. Additionally, replacement of 4-cyanobenzoyl chloride with other substituted 4-cyanobenzoyl chlorides provides compounds of formula I in which $R^{1a}$ is halogen, alkyl, haloalkyl, alkoxy, and the like.

With reference to Scheme 1, amide formation between 5-fluoro-2-nitrobenzoic acid (i) and 2-amino-5-chloropyridine in the presence of POCl₃ provides ii. Treatment of ii with methyl thioglycolate in the presence of cesium carbonate provides the thioether derivative iii. Reduction of the nitro group present in iii can be efficiently accomplished with tin(II) chloride dihydrate to produce the amine iv, which when treated with 4-cyanobenzoyl chloride provides the triaryl scaffold v. A three-step conversion of the nitrile present in v to a N,N-dimethylamidine can be accomplished using hydrogen sulfide in pyridine, followed by methyl iodide in acetone and finally dimethylamine in methanol and acetic acid to provide vi. Saponification of the methyl ester vi to the acid vii is readily accomplished using aqueous lithium hydroxide in methanol. Conversion of the carboxylic acid vii to either a N,N-dimethylamide (shown as compound viii) or a general amide (shown as ix) proceeds smoothly using an appropriate amine or cyclic amine (e.g., piperidine, morpholine and the like) and standard coupling conditions.

Scheme 1
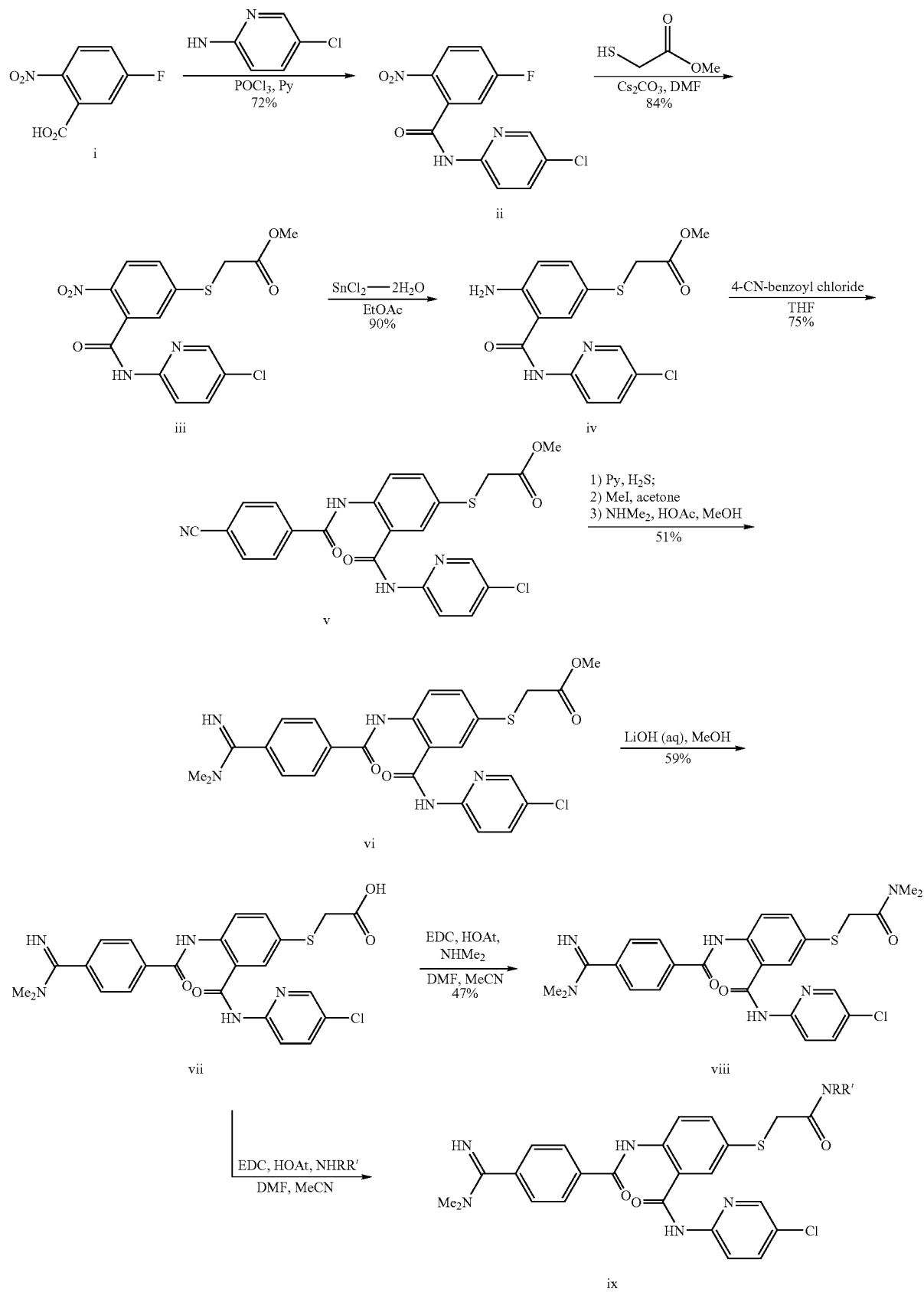

Using slight variations of the methods provided in Scheme 1, cyclic amidines (e.g, x, xi, xii and xiii) can be prepared as outlined in Scheme 2.

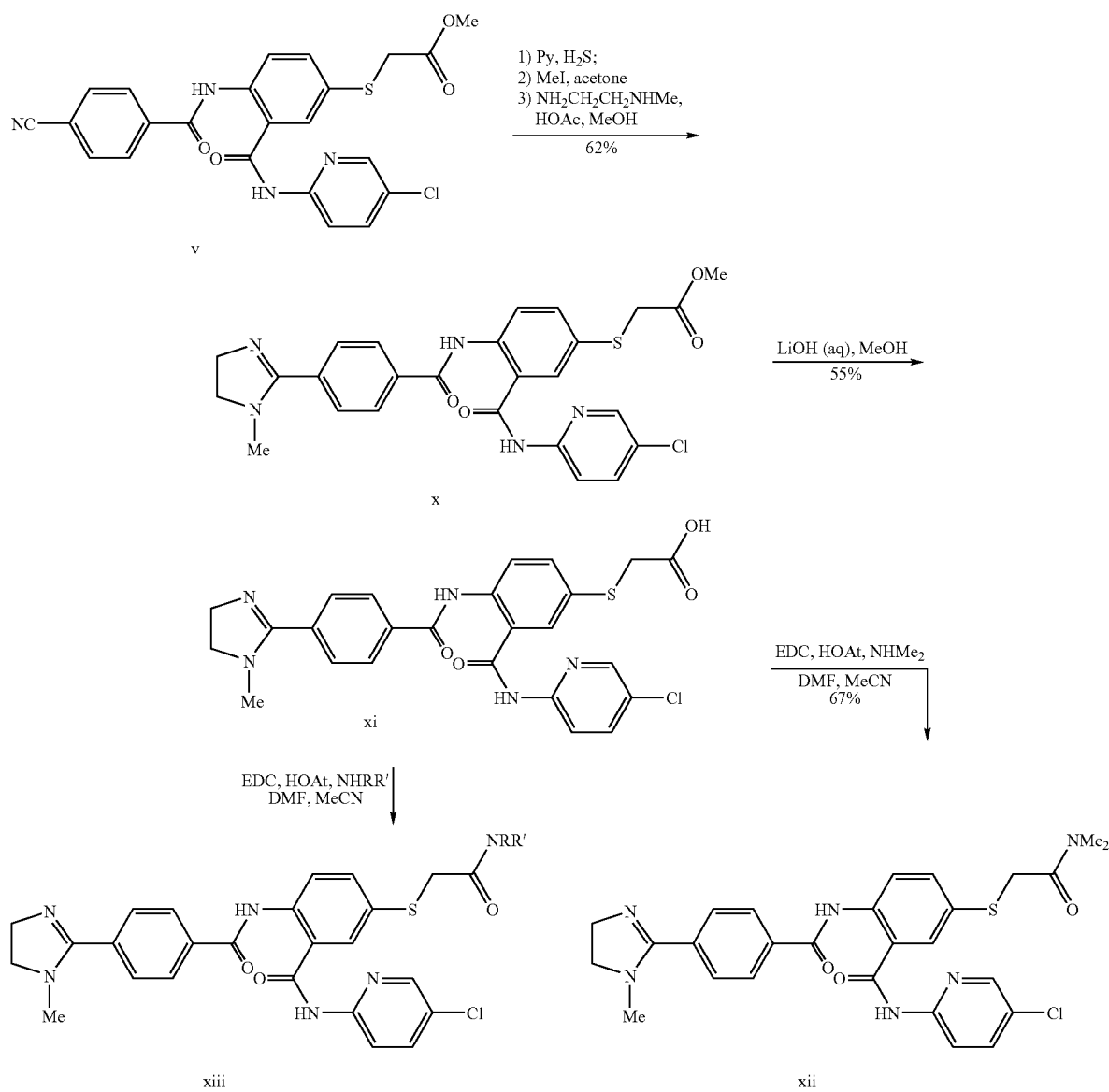

While the above schemes can be readily adapted by one of skill in the art to prepare other compounds of the present invention, reference is provided to the Examples below for a more complete discussion of solvent, amounts and ratios of reagents and other reaction conditions for the preparation of the claimed compounds.

Compositions

In another aspect of the invention, pharmaceutical compositions are provided in which compounds of Formula I, alone or in combination, are combined with a pharmaceutically acceptable carrier.

The pharmaceutical compositions of the invention may be in the form of solutions or suspensions. In the management of thrombotic disorders the compounds or pharmaceutical compositions of the invention may also be in such forms as, for example, tablets, capsules or elixirs for oral administration, suppositories, sterile solutions or suspensions or injectable administration, and the like, or incorporated into shaped articles.

Typical adjuvants which may be incorporated into tablets, capsules and the like include, but are not limited to, binders such as acacia, corn starch or gelatin, and excipients such as microcrystalline cellulose, disintegrating agents like corn starch or alginic acid, lubricants such as magnesium stearate, sweetening agents such as sucrose or lactose, or flavoring agents. When a dosage form is a capsule, in addition to the above materials it may also contain liquid carriers such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

Additionally, dosage formulations of compounds of Formula I, or pharmaceutical compositions containing a compound of the invention, to be used for therapeutic administration must be sterile. Sterility can be readily accomplished by filtration through sterile membranes such as 0.2 micron membranes, or by other conventional methods. Formulations typically will be stored in a solid form, preferably in a lyophilized form. While the preferred route of administration is orally, the dosage formulations of compounds of Formulae I, or pharmaceutical compositions of the invention may also be administered by injection, intravenously (bolus and/or infusion), subcutaneously, intramuscularly, colonically, rectally, nasally, transdermally or intraperitoneally. A variety of dosage forms may be employed as well including, but not limited to, suppositories, implanted pellets or small cylinders, aerosols, oral dosage formulations and topical formulations such as ointments, drops and dermal patches. The compounds of Formula I, and pharmaceutical compositions of the invention may also be incorporated into shapes and articles such as implants which may employ inert materials such biodegradable polymers or synthetic silicones as, for example, SILASTIC, silicone rubber or other polymers commercially available. The compounds and pharmaceutical compositions of the invention may also be provided in the form of liposome delivery systems, such as small unilamellar vesicles, large unilamellar vesicles and multilamellar vesicles. Liposomes can be formed from a variety of lipids, such as cholesterol, stearylamine or phosphatidylcholines, used methods well known to one of skill in the art. Methods of Treatment/Administration In yet another aspect, the present invention provides methods for treating or reducing the risk of thrombosis in a mammal by administering to the mammal a therapeutically effective amount of a compound of Formula I, alone or as part of a pharmaceutical composition of the invention as described above. Compounds of Formula I, and pharmaceutical compositions of the invention containing a compound of Formula I, of the invention are suitable for use alone or as part of a multi-component treatment regimen for the prevention or treatment of cardiovascular diseases, particularly those related to thrombosis. For example, a compound or pharmaceutical composition of the invention may be used as a drug or therapeutic agent for any thrombosis, particularly a platelet-dependent thrombotic indication, including, but not limited to, acute myocardial infarction, unstable angina, chronic stable angina, transient ischemic attacks, strokes, peripheral vascular disease, preeclampsia/eclampsia, deep venous thrombosis, embolism, disseminated intravascular coagulation and thrombotic cytopenic purpura, thrombotic and restenotic complications following invasive procedures, e.g., angioplasty, carotid endarterectomy, post CABG (coronary artery bypass graft) surgery, vascular graft surgery, stent placements and insertion of endovascular devices and protheses.

Compounds and pharmaceutical compositions of the invention may also be used as part of a multi-component treatment regimen in combination with other therapeutic or diagnostic agents in the prevention or treatment of thrombosis in a mammal. In certain preferred embodiments, compounds or pharmaceutical compositions of the invention may be coadministered along with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin. Coadministration may also allow for application of reduced doses of the thrombolytic agents and therefore minimize potential hemorrhagic side-effects. Compounds and pharmaceutical compositions of the invention may also act in a synergistic fashion to prevent reocclusion following a successful thrombolytic therapy and/or reduce the time to reperfusion.

The compounds and pharmaceutical compositions of the invention may be utilized in vivo, ordinarily in mammals such as primates, (e.g., humans), sheep, horses, cattle, pigs, dogs, cats, rats and mice, or in vitro. The biological properties, as defined above, of a compound or a pharmaceutical composition of the invention can be readily characterized by methods that are well known in the art such as, for example, by in vivo studies to evaluate antithrombotic efficacy, and effects on hemostasis and hematological parameters.

Subjects (typically mammalian) in need of treatment using the compounds or pharmaceutical compositions of the invention may be administered dosages that will provide optimal efficacy. The dose and method of administration will vary from subject to subject and be dependent upon such factors as the type of mammal being treated, its sex, weight, diet, concurrent medication, overall clinical condition, the particular compound of Formula I, employed, the specific use for which the compound or pharmaceutical composition is employed, and other factors which those skilled in the medical arts will recognize.

Therapeutically effective dosages may be determined by either in vitro or in vivo methods. For each particular compound or pharmaceutical composition of the invention, individual determinations may be made to determine the optimal dosage required. The range of therapeutically effective dosages will be influenced by the route of administration, the therapeutic objectives and the condition of the patient. For injection by hypodermic needle, it may be assumed the dosage is delivered into the bodily fluids. For other routes of administration, the absorption efficiency must be individually determined for each compound by methods well known in pharmacology. Accordingly, it may be necessary for the therapist to titer the dosage and modify the route of administration as required to obtain the optimal therapeutic effect.

The determination of effective dosage levels, that is, the dosage levels necessary to achieve the desired result, i.e., inhibition of Factor Xa, will be readily determined by one skilled in the art. Typically, applications of a compound or pharmaceutical composition of the invention are commenced at lower dosage levels, with dosage levels being increased until the desired effect is achieved. The compounds and compositions of the invention may be administered orally in an effective amount within the dosage range of about 0.01 to 1000 mg/kg in a regimen of single or several divided daily doses. If a pharmaceutically acceptable carrier is used in a pharmaceutical composition of the invention, typically, about 5 to 500 mg of a compound of Formula I, is compounded with a pharmaceutically acceptable carrier as called for by accepted pharmaceutical practice including, but not limited to, a physiologically acceptable vehicle, carrier, excipient, binder, preservative, stabilizer, dye, flavor, etc. The amount of active ingredient in these compositions is such that a suitable dosage in the range indicated is obtained.

The following preparations and examples are given to enable those skilled in the art to more clearly understand and to practice the present invention. They should not be considered as limiting the scope of the invention, but merely as being illustrative and representative thereof.

EXAMPLES

Example 1

This example illustrates the preparation of N-(5-chloro-2-pyridinyl)-2-(4-N,N-dimethylamidinophenylcarbonyl) amino-5-acetic acid dimethylamide sulfanyl-phenylcarboxamide

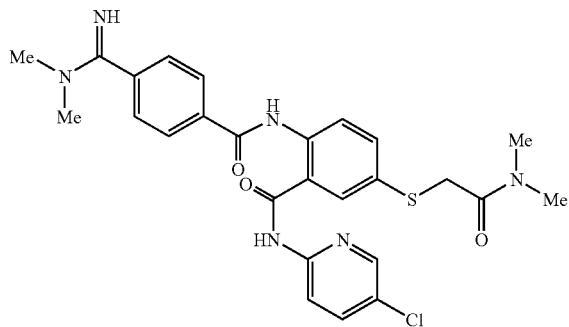

Step 1: A solution of 5-fluoro-2-nitrobenzoic acid (10.0 g, 54 mmol, 1.0 equiv.), 2-amino-5-chloropyridine (9.02 g, 1.3 equiv.), in 80 mL of pyridine was treated with phosphorous oxychloride (25.3 g, 3.0 equiv.) for 30 minutes. The volatile was evaporated and the residue was redissolved into EtOAc, washed with 1N HCl, saturated aqueous $NaHCO_3$ and saturated aqueous NaCl. The organic layer was dried over $Na_2SO_4$, filtered, and evaporated. The product was triturated with diethyl ether to give N-(5-chloro-2-pyridinyl)-(2-nitro)-5-fluorophenylcarboxamide (11.5 g, 72%). MS found for $C_{12}H_7ClFN_3O$ $(M+H)^+$: 296, (M+2+H): 298.

Step 2: A solution of N-(5-chloro-2-pyridinyl)-(2-nitro)-5-fluorophenylcarboxamide (0.60 g, 2.03 mmol, 1.0 equiv.) in 10 mL of DMF was treated with methyl thioglycolate (0.24 grams, 1.1 equiv.) and cesium carbonate (1.65 g, 2.5 equiv.) for 30 minutes at 50° C. The reaction was added to 40 mL water. The product was then extracted into EtOAc and washed with 1N HCl and saturated aqueous NaCl. The organic layer was dried over $Na_2SO_4$, filtered, and evaporated to give N-(5-chloro-2-pyridinyl)-(2-nitro)-5-acetic acid methyl ester sulfanyl-phenylcarboxamide (0.65 g, 84%). MS found for $C_{15}H_{12}ClN_3O_5S_1$ $(M+H)^+$: 382, (M+2+H): 384

Step 3: A solution of N-(5-chloro-2-pyridinyl)-(2-nitro)-5-acectic acid methyl ester sulfanyl-phenylcarboxamide (0.62 g, 1.63 mmol, 1.0 equiv.) in 10 mL of ethyl acetate was treated with tin(II) chloride-dihydrate (1.83 g, 5.0 equiv.) for 30 minutes at reflux. The solution was cooled to room temperature and added to 40 mL of 1:1 mixture of saturated aqueous sodium carbonate/saturated aqueous sodium sulfate. The resulting precipitate was filtered away. The organic layer was washed w/saturated aqueous sodium chloride, dried over $Na_2SO_4$, filtered, and evaporated to give (2-amino-5-acetic acid methyl ester sulfanyl-phenyl)-N-(5-chloro(2-pyridyl))carboxamide (0.51 g, 90%). MS found for $C_{15}H_{14}ClN_3O_3S_1$ $(M+H)^+$: 352, (M+2+H): 354.

Step 4: To a solution of (2-amino-5-acetic acid methyl ester sulfanyl-phenyl)-N-(5-chloro(2-pyridyl))carboxamide (0.50 g, 1.42 mmol, 1.0 equiv.) in 10 mL of anhydrous tetrahydrofuran was added 4-cyanobenzoyl chloride (0.28 g, 1.2 equiv.) at room temperature. After 30 minutes, the resulting precipitous slurry was diluted with 10 mL of hexanes and filtered to give N-(5-chloro(2-pyridyl)){5-acetic acid methyl ester sulfanyl-2-[(4-cyanophenyl)carbonylamino]phenyl}carboxamide (0.52 g, 75%). MS found for $C_{21}H_{15}ClN_4O_2S_1$ $(M+H)^+$: 481, $(M+2+H)^+$: 483.

Step 5: A suspension of N-(5-chloro(2-pyridyl)){5-acetic acid methyl ester sulfanyl-2-[(4-cyanophenyl) carbonylamino]phenyl}carboxamide (500 mgs, 1.04 mmol, 1.0 equiv), in 12 mL of 5:1 pyridine/triethylamine was stirred at room temperature while bubbling hydrogen sulfide gas into the mixture for over 10 minutes. After 3 hours, the volatiles were evaporated and the solid was re-suspended in 4 mL of acetone. To this mixture was added iodomethane (0.12 mL, 8.0 eq). The suspension was refluxed for 1.5 hours, and the volatile was evaporated to give N-(5-chloro(2-pyridyl)){5-acetic acid methyl ester sulfanyl-2-[(4-(iminomethylthiomethyl)phenyl)carbonylamino]phenyl}carboxamide. The crude material was carried forward immediately Step 6: To a suspension of N-(5-chloro(2-pyridyl)){5-acetic acid methyl ester sulfanyl-2-[(4-(iminomethylthiomethyl) phenyl)carbonylamino]phenyl}carboxamide (based on previous step; 0.52 mmol, 1.0 equiv.), in 6 mL of methanol was added a pre-mixed solution of glacial acetic acid (0.37 mL, 12.0 equiv.) and dimethylamine (2N in THF) (1.56 mL, 6.0 equiv.) in 4 mL of methanol. The reaction was stirred at reflux for 40 minutes and the volatiles were then evaporated. The crude mixture was purified by HPLC (C18 reverse phase) eluting with 0.1% TFA in $H_2O/CH_3CN$ to give N-(5-chloro-2-pyridinyl)-2-(4-N,N-dimethylamidinophenylcarbonyl)amino-5-acetic acid methyl ester sulfanyl-phenylcarboxamide (140 mgs, 51%). MS found for $C_{23}H_{22}Cl_1N_5O_2S_1$ $(M+H)^+$: 526, $(M+2+H)^+$: 528.

Step 7: A solution of N-(5-chloro-2-pyridinyl)-2-(4-N,N dimethylamidinophenyl carbonyl) amino-5-acetic acid methyl ester sulfanyl-phenylcarboxamide (95 mgs, 0.181 mmol, 1.0 equiv.) in 5 mL of a 1:1 mixture of water and methanol was treated with lithium hydroxide-monohydrate (19 mgs, 2.5 equiv.) for 30 minutes at room temperature. The volatile materials were evaporated. The aqueous solution was treated with 1N HCl and the resulting precipitate was filtered, dried, and collected to give N-(5-chloro-2-pyridinyl)-2-(4-N,N-dimethylamidinophenylcarbonyl)amino-5-acetic acid sulfanyl-phenylcarboxamide (55 mgs, 59%). MS found for $C_{24}H_{22}ClN_5O_4S_1$ $(M+H)^+$: 512, (M+2+H): 514.

Step 8: A suspension of N-(5-chloro-2-pyridinyl)-2-(4-N,N dimethylamidinophenyl carbonyl) amino-5-acetic acid sulfanyl-phenylcarboxamide (40 mgs, 0.078 mmol, 1.0 equiv.) in 5 mL of acetonitrile and 1 mL DMF was treated with EDC (45 mgs, 3.0 equiv.), HOAT (16 mgs, 1.5 equiv.), dimethylamine-HCl (32 mgs, 5.0 equiv.), and N-methylmorpholine (79 mgs, 10 equiv.) for 2 hrs. at 60° C. The volatile materials were evaporated and the crude mixture was purified by HPLC (C18 reverse phase) eluting with 0.1% TFA in $H_2O/CH_3CN$ to give N-(5-chloro-2-pyridinyl)-2-(4-N,N dimethylamidinophenyl carbonyl) amino-5-acetic acid dimethyl amide sulfanyl-phenylcarboxamide (20 mgs, 47%). MS found for $C_{26}H_{27}ClN_6O_3S_1$ $(M+H)^+$: 539, (M+2+H): 541.

Examples 2–9

The following compounds were prepared according to the overall procedures described above.

EXAMPLE 2

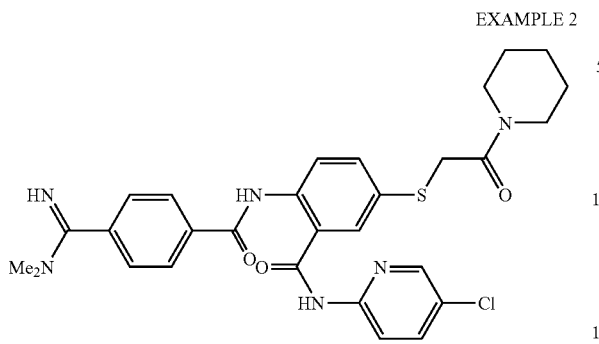

EXAMPLE 3

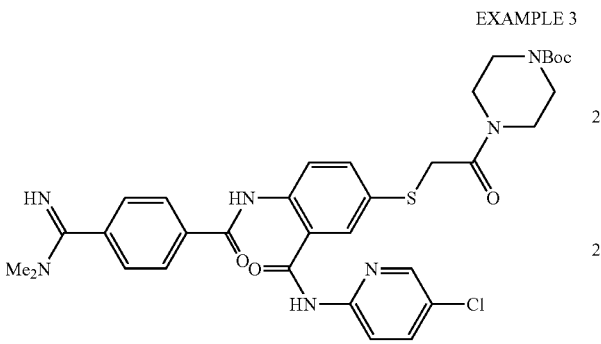

EXAMPLE 4

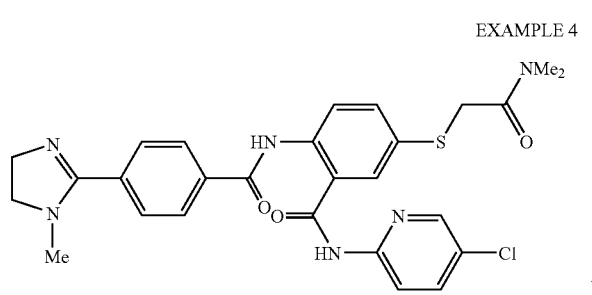

EXAMPLE 5

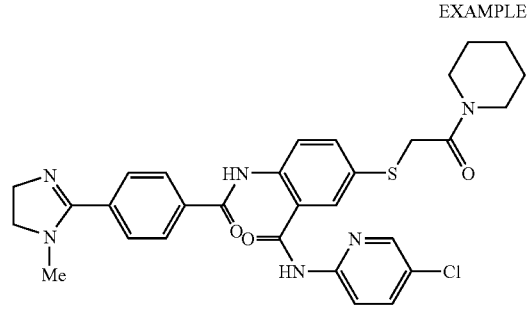

EXAMPLE 6

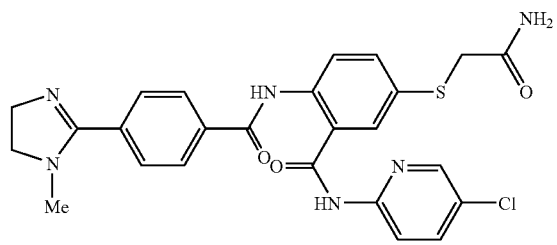

-continued

EXAMPLE 7

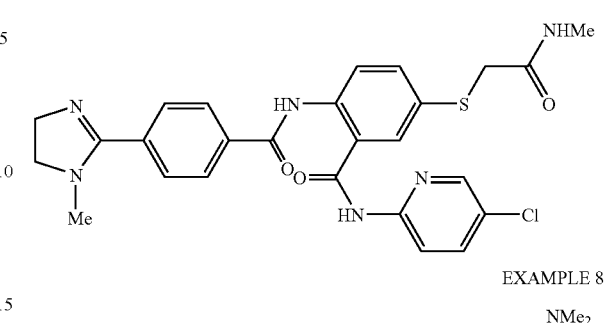

EXAMPLE 8

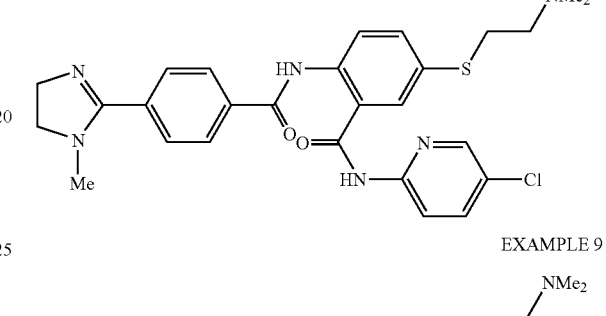

EXAMPLE 9

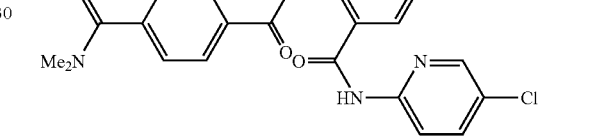

Example 10

This example provides biological activity for representative compounds of the invention. The compounds were evaluated for their ability to inhibit Factor Xa, as well as inhibit hERG. In the table below activity is represented as follows: (for Ki, factor Xa), +++ indicates a value of less than 10 nM; (for Ki, hERG), activity is indicated either as >10 micromolar or <10 micromolar.

TABLE 1

| Factor Xa Ki and hERG Ki data for Examples 1–9: | | |
|---|---|---|
| EXAMPLE | Ki, factor Xa | Ki, hERG |
| 1 | +++ | >10 μM |
| 2 | +++ | <10 μM |
| 3 | +++ | <10 μM |
| 4 | +++ | >10 μM |
| 6 | +++ | >10 μM |
| 7 | +++ | >10 μM |
| 9 | +++ | >10 μM |

The examples in Table 1 above show that the present compounds are potent inhibitors of factor Xa while having relatively weak hERG binding. In the hERG binding assay, almost all of the compounds tested provided a Ki of greater than 1.0 micromolar and many were greater than 10 micromolar. This desirable selectivity is an improvement over the selectivity of other factor Xa inhibitors that have a related chemical structure. It was found that the —SCH$_2$C(=X)N(R$^{1b}$)(R$^{1c}$) moiety attached to the middle ring of the formula I compounds was a critical feature for the improved selectivity. By comparison, the majority of factor Xa compounds tested that were lacking the —SCH$_2$C(=X)N(R$^{1b}$)(R$^{1c}$) moiety provided hERG binding below 1.0 micromolar. For the present compounds the ratio of Ki (hERG)/Ki (factor Xa) ranges from about 4000 to greater than about 80,000. Preferably the ratio is greater than about 10,000.

Assays above were conducted as described below:

Protocol for Assay of Factor Xa Inhibitors

IC$_{50}$ and Ki Determinations:

Substrate:

The substrate S-2765 (Z-D-Arg-Gly-Arg-pNA.HCl) was obtained from Diapharma (West Chester, Ohio).

Enzyme:

The human plasma protein factor Xa was purchased from Haematologic Technologies (Essex Junction, Vt.).

Methods

IC$_{50}$ Determinations

All assays, which are performed in 96-well microtiter plates, measure proteolytic activity of the enzyme (factor Xa) by following cleavage of paranitroanilide substrate. The assay buffer used for proteolytic assays was Tris buffered saline (20 mM Tris, 150 mM NaCl, 5 mM CaCl$_2$, 0.1% Bovine serum albumin (BSA), 5% Dimethly Sulfoxide (DMSO) pH 7.4). In a 96-well microtiter plate, inhibitor was serially diluted to give a range of concentrations from 0.01 nM to 10 µM (final). Duplicate sets of wells were assayed and control wells without inhibitor were included. Enzyme was added to each well,(fXa concentration=1 nM), the plate was shaken for 5 seconds and then incubated for 5 minutes at room temperature. S2765 was added (100 µM final) and the plate was shaken for 5 seconds (final liquid volume in each well was 200 µl). The degree of substrate hydrolysis was measured at 405 nm on a Thermomax plate reader (Molecular Devices, Sunnyvale, Calif.) for 2 minutes. The initial velocities (mOD/min), for each range of inhibitor concentrations, were fitted to a four parameter equation using Softmax data analysis software. The parameter C, derived from the resulting curve-fit, corresponded to the concentration for half maximal inhibition (IC$_{50}$).

K$_i$ Determination

The assay buffer for this series of assays was: Hepes buffered saline (20 mM Hepes, 150 mM NaCl, 5 mM CaCl$_2$, 0.1% PEG-8000, pH 7.4). In a 96-well microtiter plate, inhibitor was serially diluted in a duplicate set of wells to give a range of final concentrations from 5 pM to 3 µM final. Controls without inhibitor (8 wells) were included. The enzyme, fXa (1 nM final) was added to the wells. The substrate S-2765 (200 µM final) was added and the degree of substrate hydrolysis was measured at 405 nm on a Thermomax plate reader for 5 minutes, using Softmax software. Initial velocities (mOD/min) were analyzed by non-linear least squares regression in the Plate Ki software (BioKin Ltd, Pullman, Wash.)(Literature reference: Kusmic P, et al., "High-throughput screening of enzyme inhibitors: Automatic determination of tight-binding inhibition constants" *Anal. Biochemistry* 2000, 281:62–67). The model used for fitting the inhibitor dose-response curves was the Morrison equation. An apparent K$_i$ (Ki*) was determined. The overall K$_i$ was calculated using the following equation:

$$Ki = \frac{Ki^*}{1 + \frac{[S]}{Km}} \text{ where } [S] \text{ is substrate concentration (200 µM)}$$

and K$_m$ the Michaelis constant for S2765.

The hERG (Human Ether-a-go-go Related Gene Protein) Membrane Binding Assay

Human embryonic kidney (HEK293) cells stably transfected with hERG cDNA were used for preparation of membranes (Literature reference: Zhou, Z., et al., "Properties of HERG stably expressed in HEK293 cells studied at physiological temperature." *Biophys. J,* 1998, 74:230–241). The assay buffer was comprised of 50 mM Tris, 10 mM KCl, 1 mM MgCl$_2$, pH 7.4. Competition assays for hERG binding were performed, in a 96 well plate, with 50 µL $^3$H-dofetilide, at a concentration of 3.5 nM (final concentration of 0.01% ethanol). Test compound was added at final concentrations of 100 µM, 33.33 µM, 11.11 µM, 3.70 µM, 1.23 µM, 0.41 µM, 0.14 µM, 0.046 µM, 0.015 µM, and 0.005 µM (1.0% DMSO). Each compound was run in duplicate on each of two plates. Total binding was determined by addition of 50 µL of assay buffer in place of compound. Non-specific binding was determined by addition of 50 µL of 50 µM terfenadine in place of test compound. All assays were initiated by addition of 150 µL of membrane homogenates (15 ug protein/well as final concentration) to the wells (total volume=250 µL per well), and the plates were incubated at room temperature for 80 minutes on a shaking platform. All assays were terminated by vacuum filtration on to glass fiber filters, followed by two washes with cold assay buffer. The filter plates were dried at 55° C. for 90 minutes, after which, Microscint 0 (50 µL) was added to each well of the dried filter plate. The plates were counted on a Packard Topcount (Perkin Elmer, Boston, Mass.) using a one minute protocol. Scintillation reading (counts per minute, CPM) data generated by the Packard TopCount was used to calculate the percent inhibition of $^3$H-dofetilide binding, for each compound at each concentration, using the total binding control value corrected for non-specific binding. The IC$_{50}$ value was calculated from the percent inhibition curve generated using Excel XL Fit software (Microsoft). The equilibrium dissociation constant (K$_i$) was calculated using the equation of Cheng and Prusoff.

$$K_i = IC_{50}/[1+([L]/K_D)]$$

(Literature reference: Cheng Y, Prusoff W H., "Relationship between the inhibition constant (Ki) and the concentration of inhibitor which causes 50 per cent inhibition (I50) of an enzymatic reaction," *Biochem Pharmacol.,* 1973, 22(23), 3099–108.

The following compounds can be prepared according to the procedures previously described.

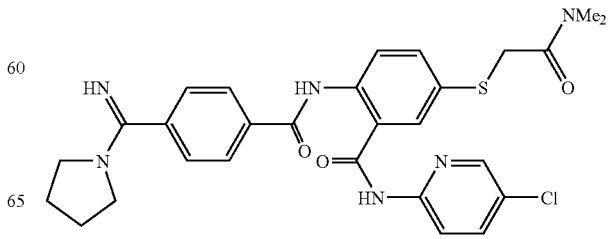

-continued
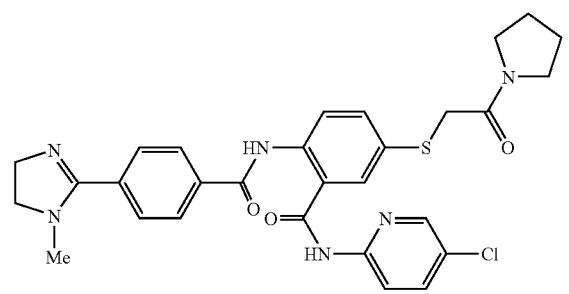
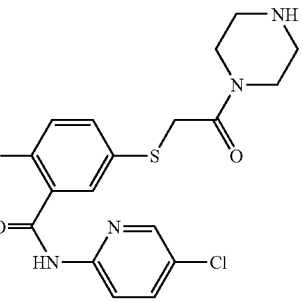
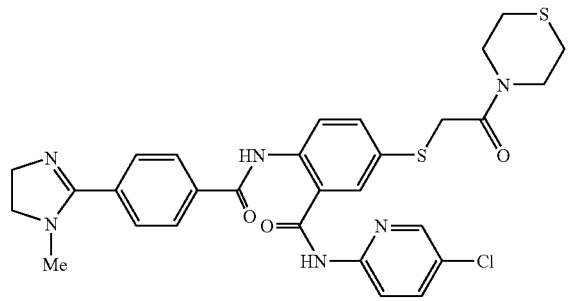
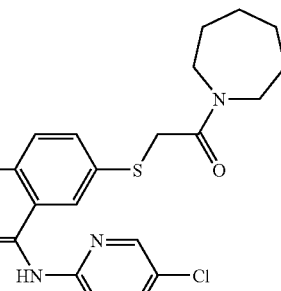
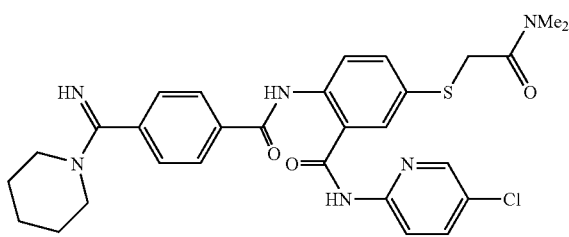
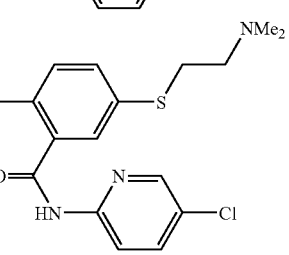
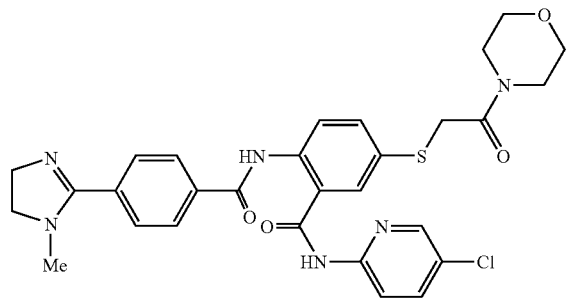
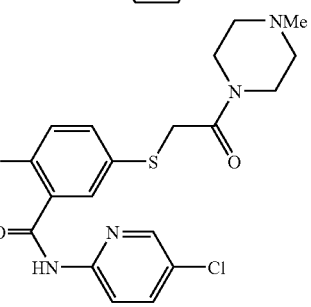
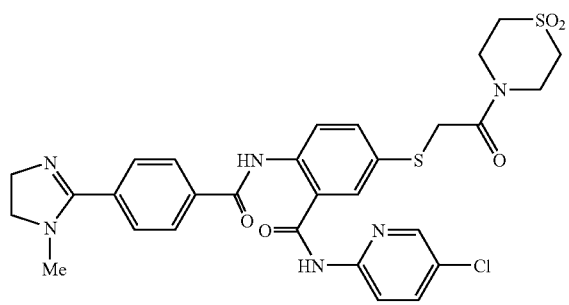
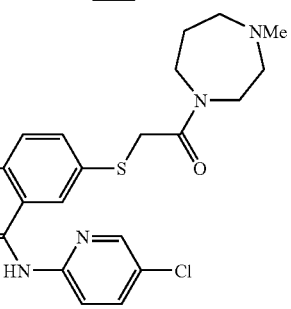
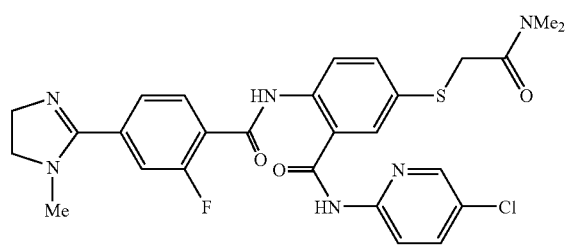
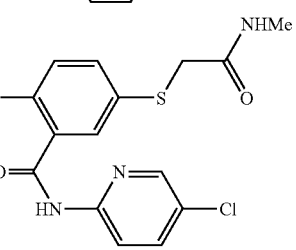

-continued

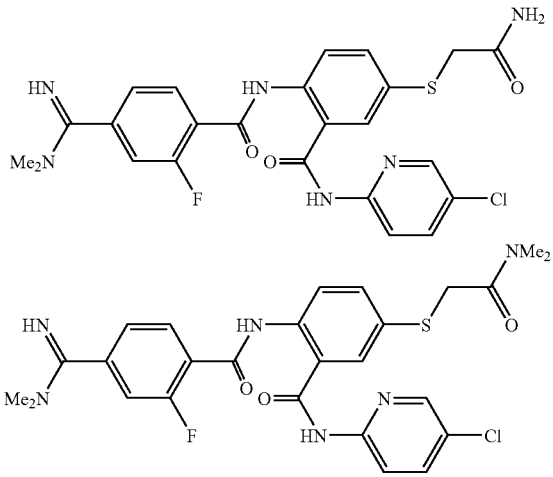

It should be understood that the foregoing discussion, embodiments and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

The invention claimed is:

1. A compound having the formula:

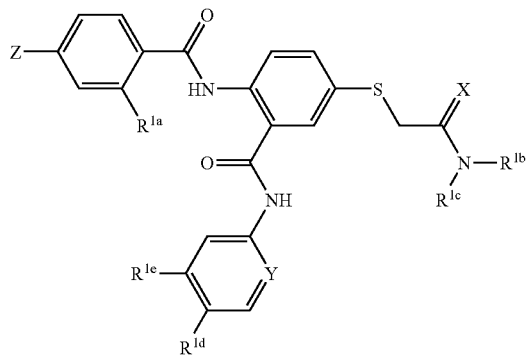

or a pharmaceutically acceptable salt thereof,
wherein
$R^{1a}$ is a member selected from the group consisting of H, halogen, hydroxy, $C_{1-6}$ alkyl, $C_{1-6}$ haloalkyl, $C_{1-6}$ alkoxy, $C_{1-6}$ haloalkoxy, $(C_{1-6}$ alkyl$)_{0-2}$amino and $C_{1-6}$ alkylcarbonyl;

$R^{1b}$ and $R^{1c}$ are each members independently selected from the group consisting of H and $C_{1-6}$ alkyl, or optionally, $R^{1b}$ and $R^{1c}$ are combined with the nitrogen atom to which each is attached to form a 5-, 6- or 7-membered monocyclic ring having from 0 to 1 additional heteroatom ring members or an 8-, 9-, 10- or 11-membered bicyclic ring having 0–2 additional heteroatom ring members, said heteroatom ring members selected from O, N, S, S(O) and S(O)$_2$, said ring being further substituted with from zero to two substituents independently selected from the group consisting of $C_{1-6}$ alkyl, $(C_{1-6}$ alkyl$)_{0-2}$amino, oxo and an amine protecting group;

$R^{1d}$ and $R^{1e}$ are each members independently selected from the group consisting of H, halogen, hydroxy, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $(C_{1-6}$ alkyl$)_{0-2}$amino and amino$C_{1-6}$ alkyl; or $R^{1d}$ and $R^{1e}$ are combined to form a fused 5–6 membered ring having 0–2 ring heteroatoms selected from N, O and S;

X is O, S or together with the carbon atom to which it is attached is CH$_2$;

Y is CH or N; and

Z is a group having the formula:

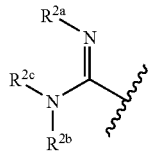

wherein
$R^{2a}$, $R^{2b}$ and $R^{2c}$ are each members independently selected from the group consisting of H, hydroxy, $C_{1-6}$ alkyl, $C_{3-6}$ cycloalkyl, $C_{1-6}$ alkoxy and $(C_{1-6}$ alkyl$)_{0-2}$amino; or optionally, any two of $R^{2a}$, $R^{2b}$ and $R^{2c}$ are taken together with their intervening atom(s) to form a 3-, 4-, 5-, 6- or 7-membered ring having from 0 to 1 additional heteroatom ring members selected from O, N, S, S(O) and S(O)$_2$, said ring being further substituted with from zero to two substituents independently selected from the group consisting of $C_{1-6}$ alkyl, hydroxy, $C_{1-6}$ alkoxy, CO$_2$H, oxo and $(C_{1-6}$ alkyl$)_{0-2}$amino.

2. The compound of claim 1, wherein X is O.

3. The compound of claim 1, wherein Y is N.

4. The compound of claim 1, wherein $R^{1a}$ is H or halogen.

5. The compound of claim 1, wherein $R^{1b}$ and $R^{1c}$ are each members independently selected from the group consisting of H and $C_{1-4}$ alkyl.

6. The compound of claim 1, wherein $R^{1d}$ is selected from the group consisting of halogen, hydroxy, $C_{1-3}$ alkyl, $C_{1-3}$ haloalkyl, $C_{1-3}$ alkoxy and amino$C_{1-3}$ alkyl.

7. The compound of claim 1, wherein X is O; and Z is a member selected from the group consisting of

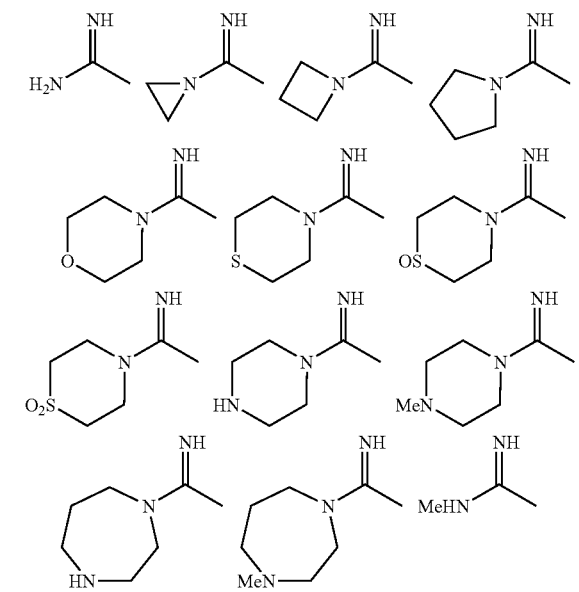

-continued

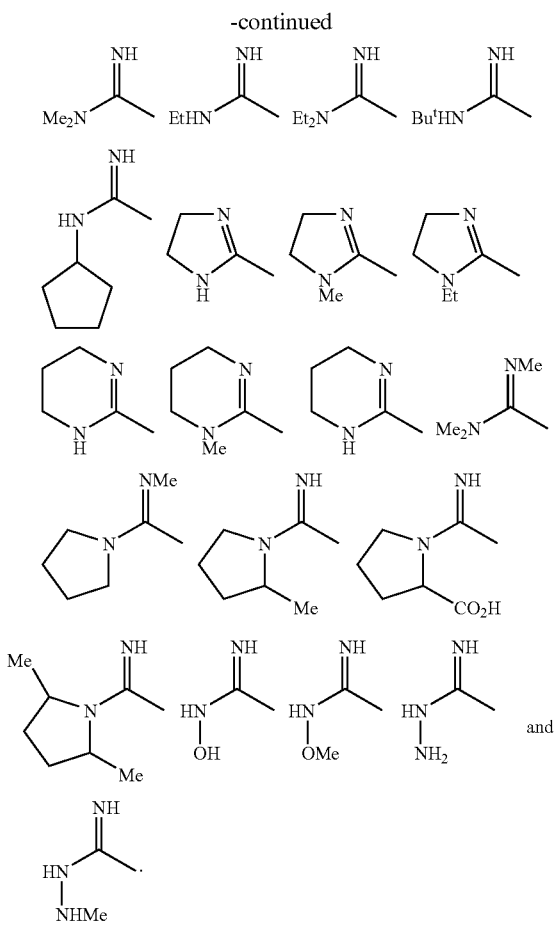

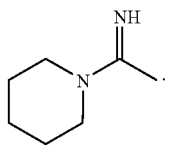

8. The compound of claim 7, wherein the moiety —N(R$^{1b}$)(R$^{1c}$) is a member selected from the group consisting of

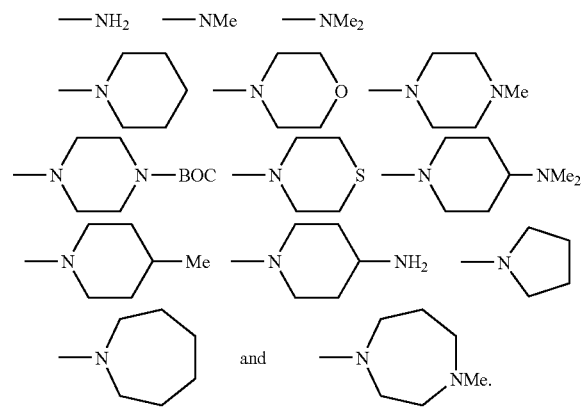

9. The compound of claim 8, wherein Z is a member selected from the group consisting of

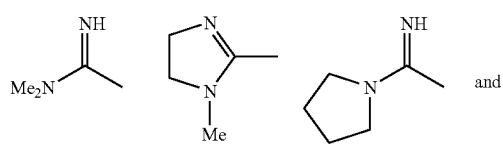

10. The compound of claim 7, wherein R$^{1a}$ is selected from the group consisting of H, F, Cl and Br.

11. The compound of claim 7, wherein Y is N; R$^{1a}$ is selected from the group consisting of H, F, Cl and Br; and R$^{1d}$ is selected from the group consisting of —F, —Cl, —Br, —OCH$_3$, —OH, —CH$_3$, —CF$_3$ and —CH$_2$NH$_2$.

12. The compound of claim 11, wherein R$^{1b}$ and R$^{1c}$ are each independently selected from the group consisting of H and C$_{1-3}$ alkyl.

13. The compound of claim 11, wherein R$^{1b}$ and R$^{1c}$ are combined with the nitrogen atom to which each is attached to form a 5-, 6- or 7-membered ring having from 0 to 1 additional heteroatom ring members selected from O, N and S, said ring being selected from the group consisting of pyrrolidine, piperidine, piperazine, morpholine, homopiperidine, homopiperazine and thiomorpholine.

14. The compound of claim 1, wherein X and the carbon atom to which it is attached is CH$_2$.

15. The compound of claim 14, wherein Z is a member selected from the group consisting of

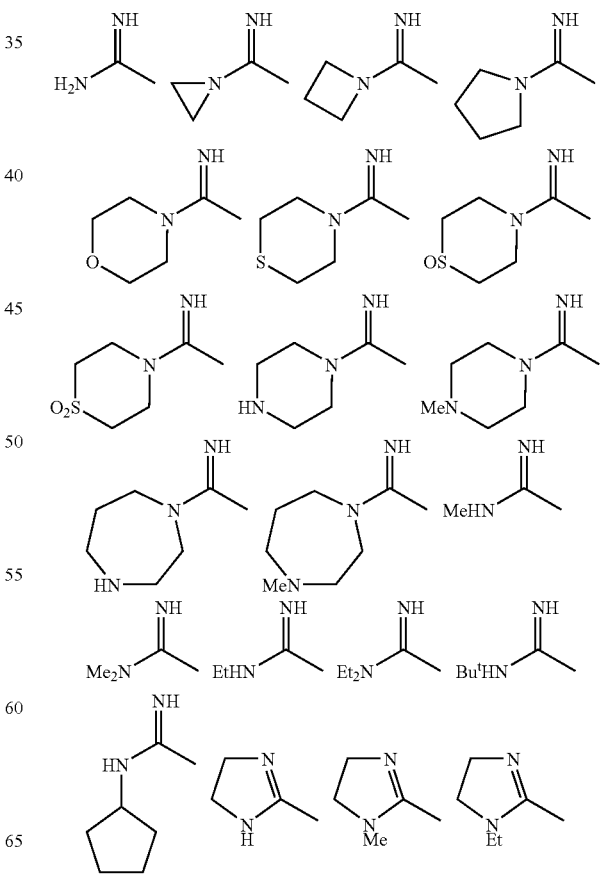

-continued

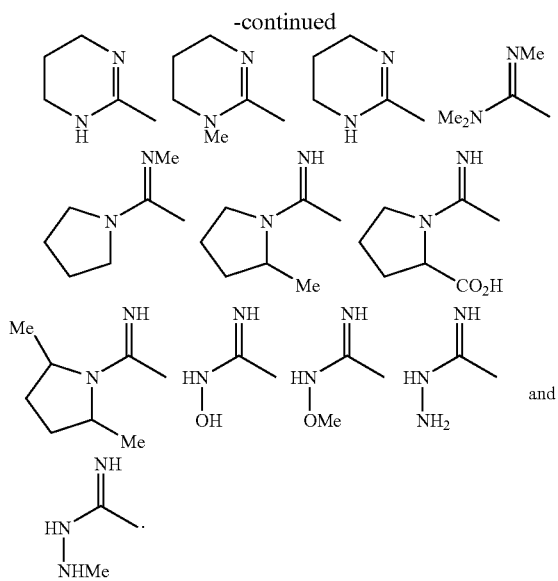

16. The compound of claim 15, wherein the moiety —N($R^{1b}$)($R^{1c}$) is a member selected from the group consisting of

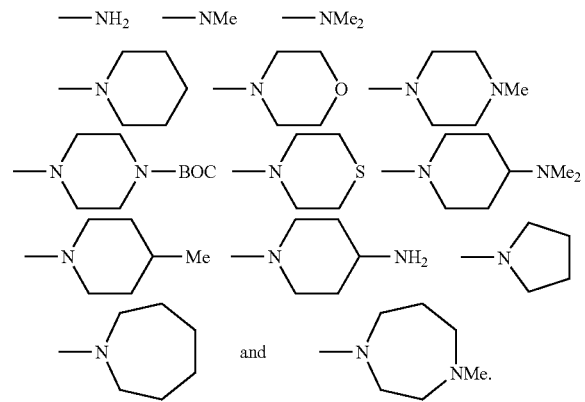

17. The compound of claim 16, wherein Z is a member selected from the group consisting of

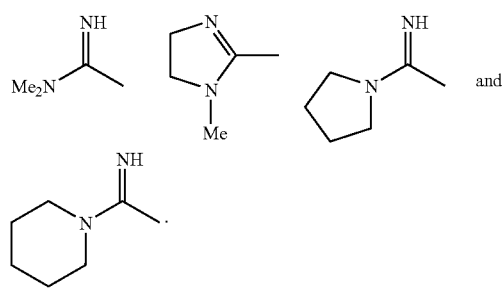

18. The compound of claim 15, wherein $R^{1a}$ is selected from the group consisting of H, F, Cl and Br.

19. The compound of claim 15, wherein Y is N; $R^{1a}$ is selected from the group consisting of H, F, Cl and Br; and $R^{1d}$ is selected from the group consisting of —F, —Cl, —Br, —OCH$_3$, —OH, —CH$_3$, —CF$_3$ and —CH$_2$NH$_2$.

20. The compound of claim 19, wherein $R^{1b}$ and $R^{1c}$ are each independently selected from the group consisting of H and $C_{1-3}$ alkyl.

21. The compound of claim 19, wherein $R^{1b}$ and $R^{1c}$ are combined with the nitrogen atom to which each is attached to form a 5-, 6- or 7-membered ring having from 0 to 1 additional heteroatom ring members selected from O, N and S, said ring being selected from the group consisting of pyrrolidine, piperidine, piperazine, morpholine, homopiperidine, homopiperazine and thiomorpholine.

22. The compound of claim 1, selected from the group consisting of

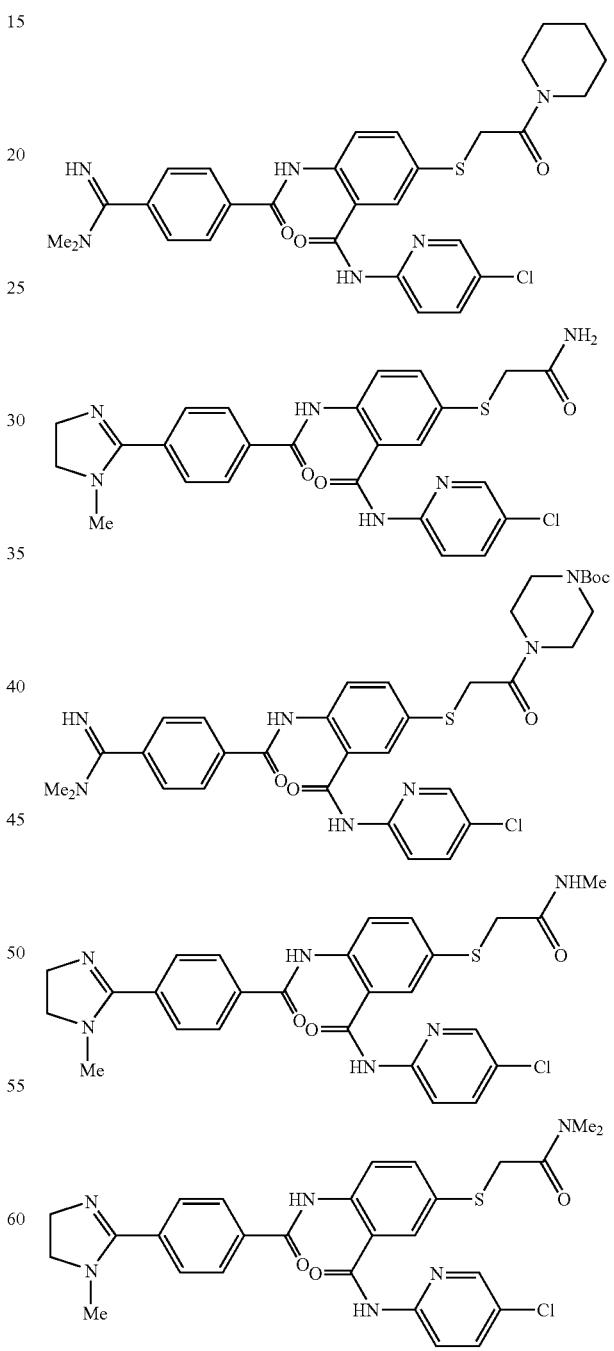

-continued
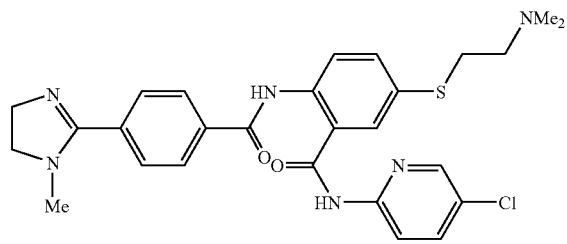
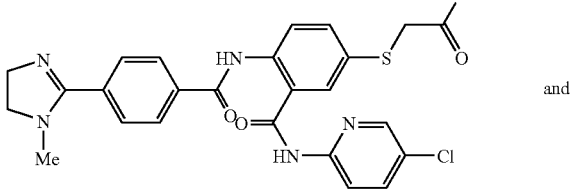
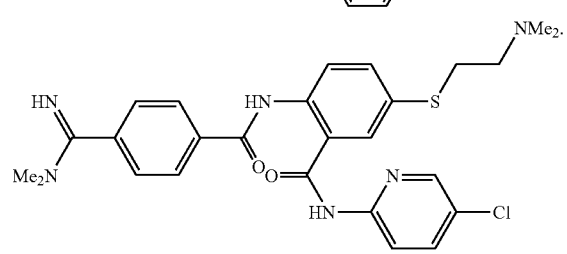
23. The compound of claim 1, selected from the group consisting of
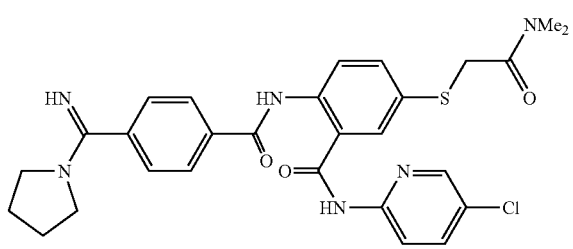
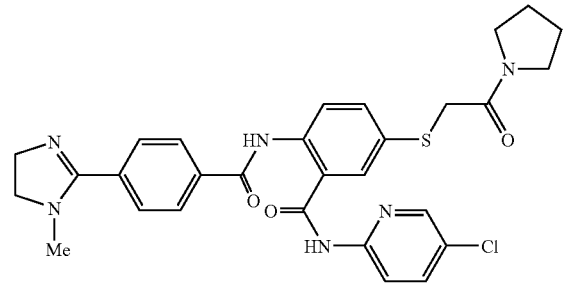
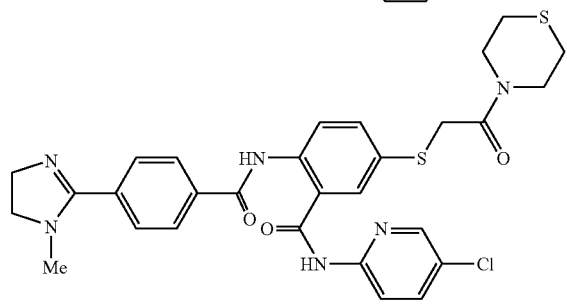
-continued
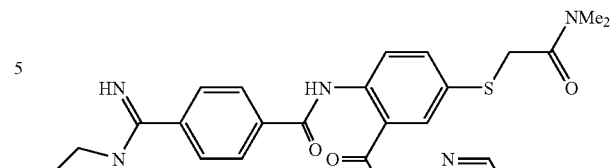
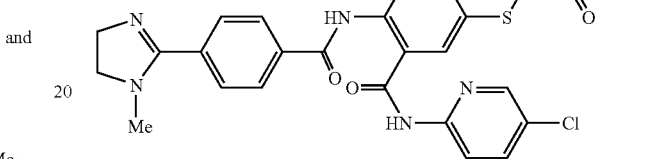
and
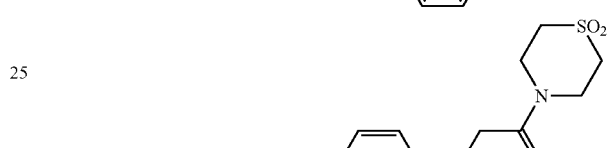
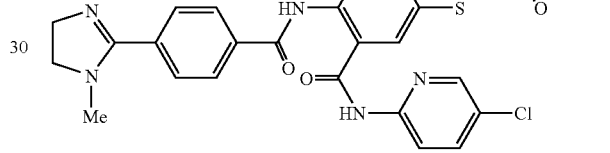
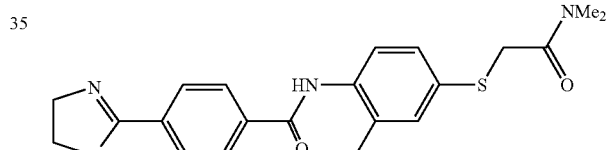
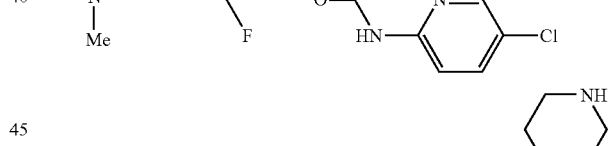
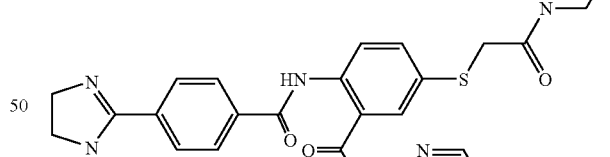
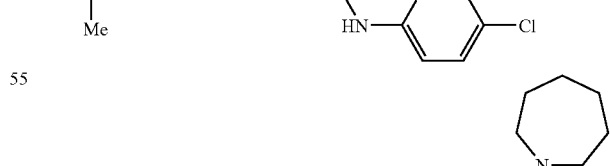
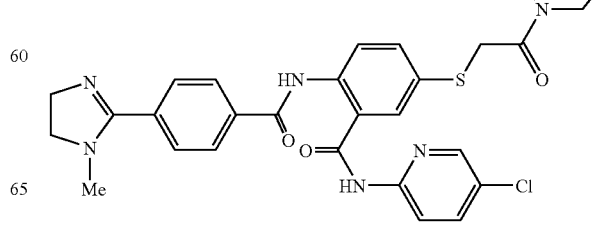

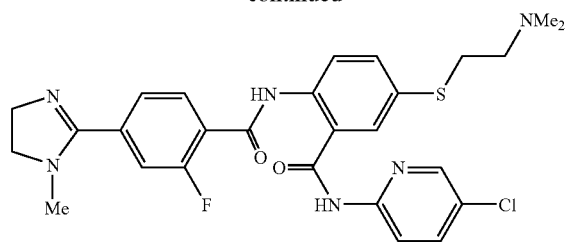
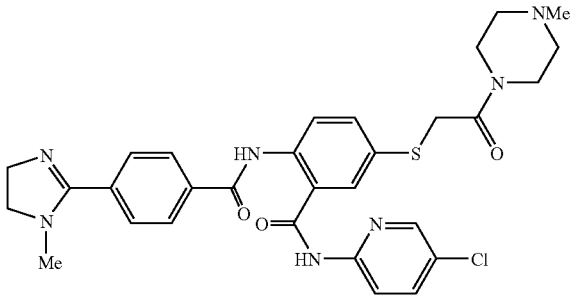
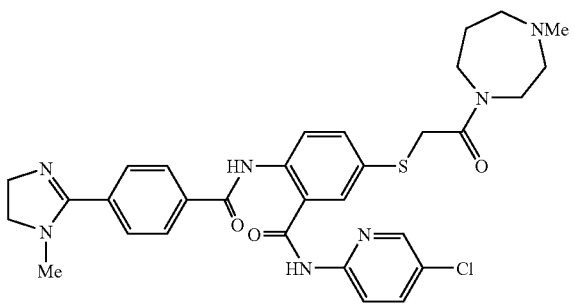
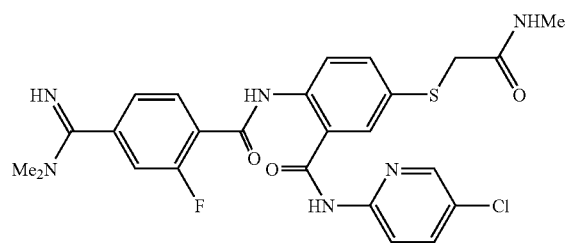
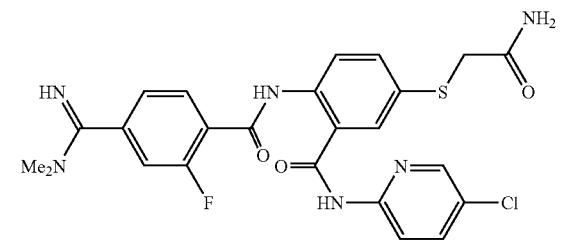

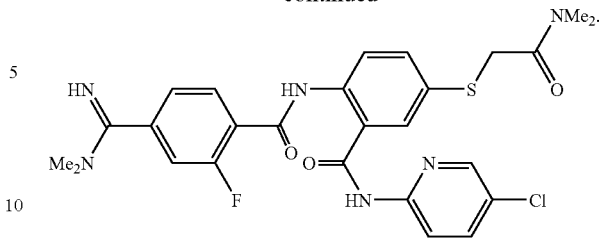

24. A composition comprising a pharmaceutically acceptable excipient and a compound of claim 1.

25. A method of treating or reducing the risk of a condition in a mammal, said condition characterized by undesired thrombosis comprising the step of administering to said mammal a therapeutically effective amount of a compound of claim 1.

26. The method in accordance with claim 25, wherein said condition is selected from the group consisting of: acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, and conditions requiring the fitting of prosthetic devices.

27. The method for inhibiting the coagulation of biological samples, comprising contacting said sample with a compound of claim 1.

28. The method in accordance with claim 25, wherein said compound is administered orally or intravenously.

29. The method in accordance with claim 25, wherein said compound is administered in combination with a stent.

30. The method in accordance with claim 25, wherein said compound is administered in combination with a second therapeutic agent.

* * * * *